(12) United States Patent
Gordon et al.

(10) Patent No.: US 8,377,097 B2
(45) Date of Patent: Feb. 19, 2013

(54) BONE TISSUE CLAMP

(75) Inventors: Charles Gordon, Tyler, TX (US); Marc Yap, The Colony, TX (US)

(73) Assignee: Osteomed, LLC, Addison, TX (US)

( * ) Notice: Subject to any disclaimer, the term of this patent is extended or adjusted under 35 U.S.C. 154(b) by 205 days.

(21) Appl. No.: 12/820,575

(22) Filed: Jun. 22, 2010

(65) Prior Publication Data

US 2011/0029020 A1 Feb. 3, 2011

Related U.S. Application Data

(60) Provisional application No. 61/219,687, filed on Jun. 23, 2009.

(51) Int. Cl.
*A61B 17/70* (2006.01)

(52) U.S. Cl. ........................ 606/248; 606/249; 623/17.11

(58) Field of Classification Search .................... 606/90, 606/246, 248, 249; 623/17.11; 923/17.11
See application file for complete search history.

(56) References Cited

U.S. PATENT DOCUMENTS

| | | | |
|---|---|---|---|
| 5,645,599 | A | 7/1997 | Samani |
| 5,836,948 | A | 11/1998 | Zucherman |
| 6,238,397 | B1 | 5/2001 | Zucherman |
| 6,440,169 | B1 | 8/2002 | Elberg |
| 2003/0040746 | A1 * | 2/2003 | Mitchell et al. ................ 606/61 |
| 2008/0183211 | A1 * | 7/2008 | Lamborne et al. ............ 606/249 |
| 2008/0228225 | A1 | 9/2008 | Trautwein |

FOREIGN PATENT DOCUMENTS

WO WO2009086397 7/2009

OTHER PUBLICATIONS

O. Bostman; *Posterior Spinal Fusion Using Internal Fixation with the Daab Plate*, Acta Orthop Scand 55, pp. 310-314, 1984, www.informahealthcare.com.
Saint John's Health Center, *Saint John's Spine Surgeon Uses ILIF Procedure to Treat Lumbar Spinal Stenosis*, www.medicalnewstoday.com/articles/155013.php.
LANX, *Aspen Spinous Process System Product Brochure*, www.lanx.com Dec. 16, 2008.
LANX, *Aspen Spinous Process System*, Microsoft Power Point Presentation, Aug. 6, 2007.

* cited by examiner

*Primary Examiner* — Eduardo C Robert
*Assistant Examiner* — Christina Negrellirodriguez
(74) *Attorney, Agent, or Firm* — Peter K. Johnson; James Larson; James Pinkston

(57) ABSTRACT

Systems, methods, and kits incorporate a fusion member for vertebral processes. The fusion member may be unitary or modular. The fusion member comprises extensions configured to be crimped to vertebral processes. The extensions may comprise tabs configured to be deformed to further penetrate the vertebral processes. The tabs may also lock together modular components of the fusion member. The fusion member may comprise fasteners extending between the extensions. The fusion member may comprise a cage with a movable cover or a graft retention feature.

66 Claims, 17 Drawing Sheets

BONE TISSUE CLAMP

CROSS-REFERENCE TO RELATED APPLICATIONS

This application claims the benefit of U.S. Application No. 61/219,687, filed Jun. 23, 2009, entitled BONE TISSUE CLAMP, which is pending.

The above-referenced document is hereby incorporated by reference in its entirety.

This application incorporates by reference each of the following applications in its entirety:

U.S. Provisional Patent Application 61/017,336, filed Dec. 28, 2007, entitled BONE TISSUE CLAMP, which is expired;

U.S. Provisional Patent Application 61/023,327, filed Jan. 24, 2008, entitled BONE TISSUE CLAMP, which is expired;

U.S. Provisional Patent Application 61/104,199, filed Oct. 9, 2008, entitled BONE TISSUE CLAMP, which is expired;

U.S. Provisional Patent Application 61/108,368, filed Oct. 24, 2008, entitled BONE TISSUE CLAMP, which is expired;

International Patent Application No. PCT/US2008/088196, filed Dec. 23, 2008, entitled BONE TISSUE FIXATION DEVICE AND METHOD, which is pending; and U.S. patent application Ser. No. 12/342,816, filed Dec. 23, 2008, entitled BONE TISSUE FIXATION DEVICE AND METHOD, which is pending.

BACKGROUND OF THE INVENTION

1. The Field of the Invention

Exemplary embodiments of the present disclosure comprise a device that can be secured to bone tissue and methods of securing the devices. In specific exemplary embodiments, a device may be secured to spinous processes of vertebral bodies. In other exemplary embodiments, a device may be secured to a calvarial flap or other bone tissue.

2. Description of Related Art

The pedicle screw is a common medical device currently used to attach components to a patient's vertebrae. While providing a stable platform to attach components to vertebrae, the pedicle screw has inherent drawbacks in its use. Such drawbacks include the difficulty in accessing the portion of the vertebrae needed to insert the pedicle screw. In addition, there are risks of serious injuries to the patient when using a pedicle screw to penetrate a vertebra in a region close to the nerves of the spinal cord.

Systems and methods for treatment for various spinal conditions have been disclosed in U.S. Pat. Nos. 5,645,599 and 6,440,169, incorporated herein by reference. Additional systems and methods of treatment have been disclosed in "Interspinous Process Decompression for Neurogenic Intermittent Claudication Secondary to Degenerative Lumbar Spinal Stenosis", Global Surgery—Future Directions 2005 by Patrick Simons, also incorporated herein by reference.

SUMMARY OF THE INVENTION

Exemplary embodiments of the present disclosure provide novel systems, kits, and methods for securing medical devices to bones for use in treatment of spinal conditions and other medical conditions where securement to bone tissue is needed.

BRIEF DESCRIPTION OF THE DRAWINGS

While exemplary embodiments of the present invention have been shown and described in detail below, it will be clear to the person skilled in the art that changes and modifications may be made without departing from the scope of the invention. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, different materials of construction may be used for the insert employed in the kit or system. Furthermore, the shape of insert may also be altered.

Figure 1:
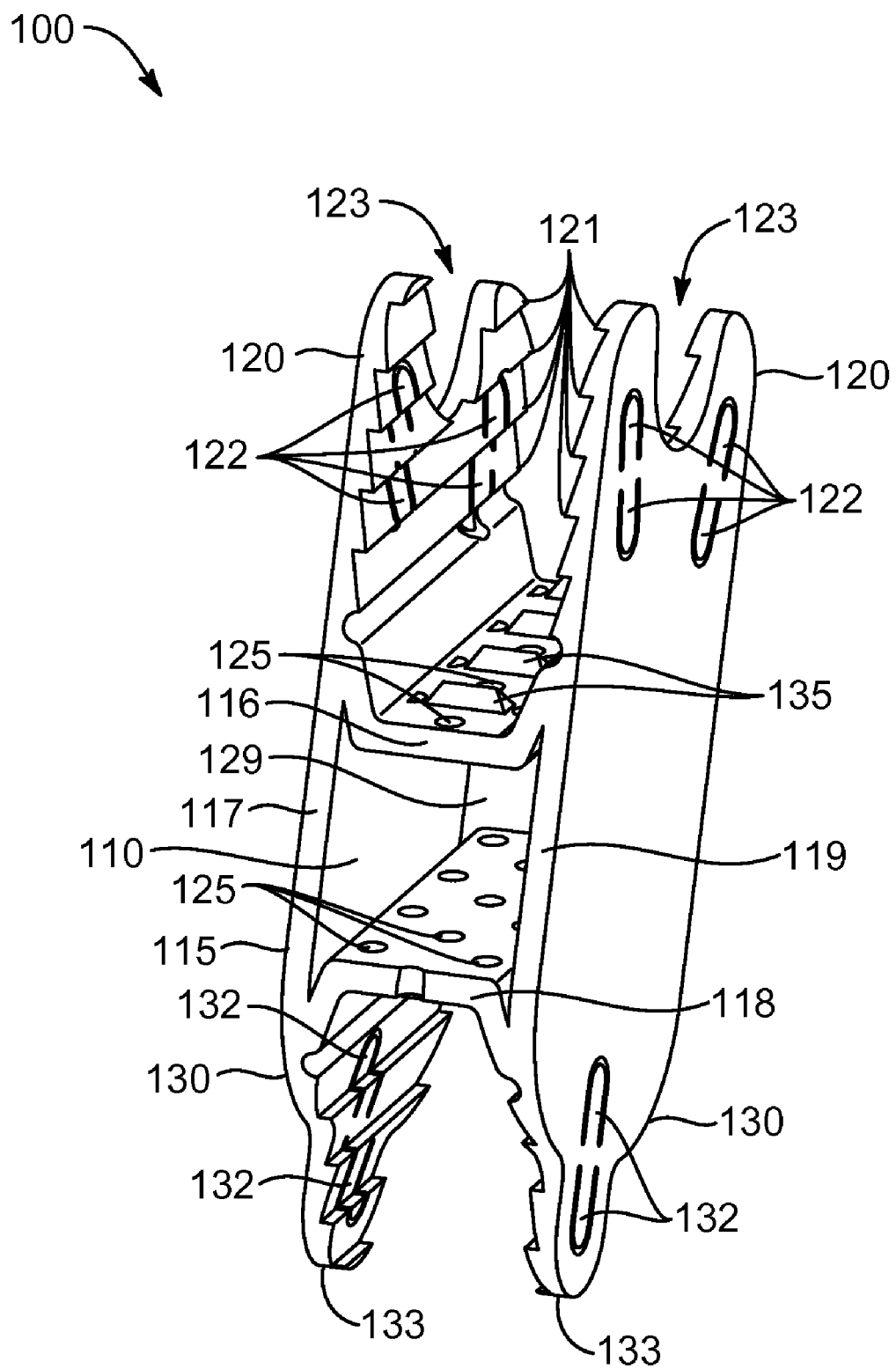

In the following Detailed Description, various features are grouped together in several embodiments for the purpose of streamlining the disclosure. This method of disclosure is not to be interpreted as reflecting an intention that exemplary embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear. Similar reference numbers (e.g., those that are identical except for the first numeral) are used to indicate similar features in different embodiments.

Figure 2:
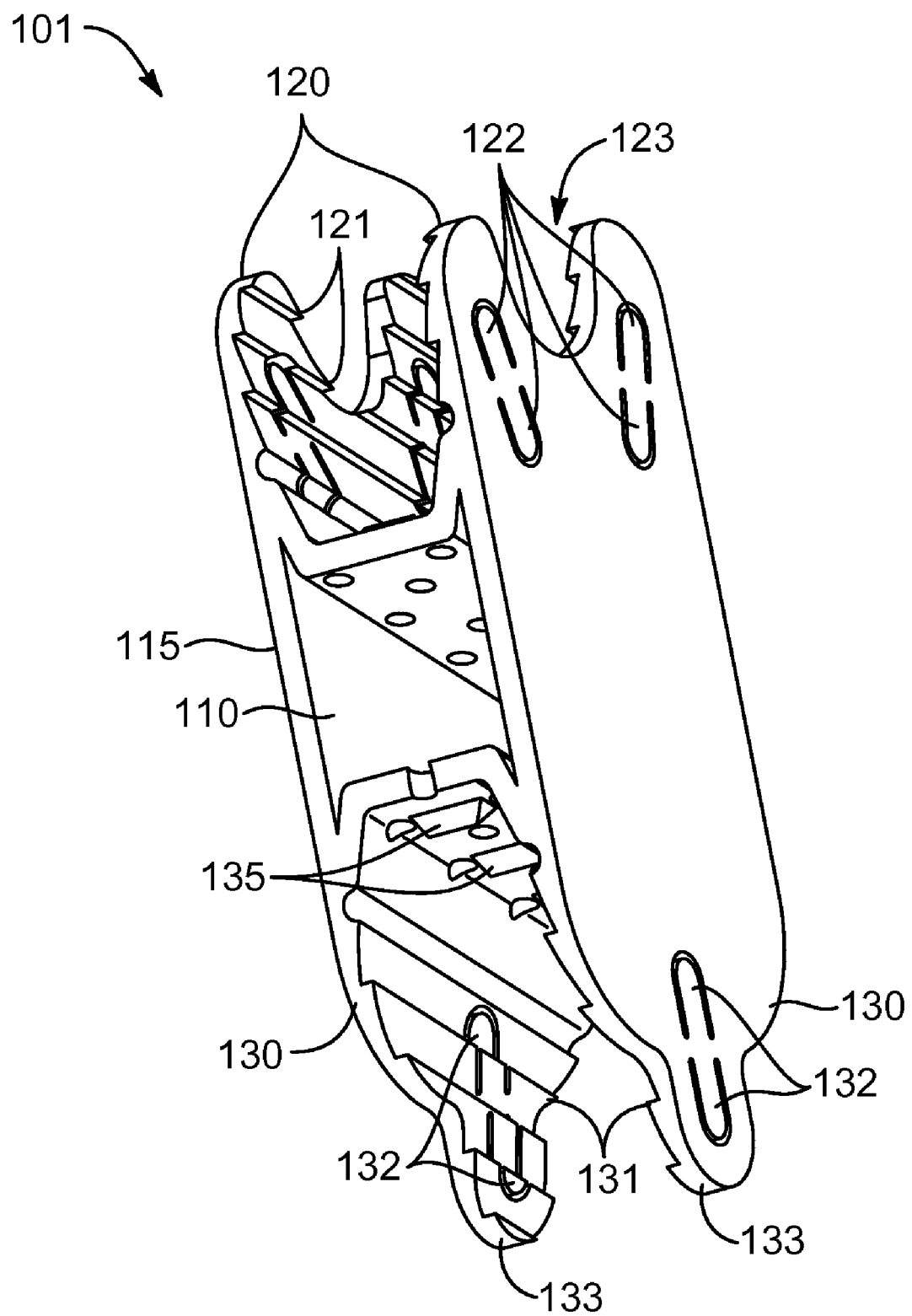
Figure 3:
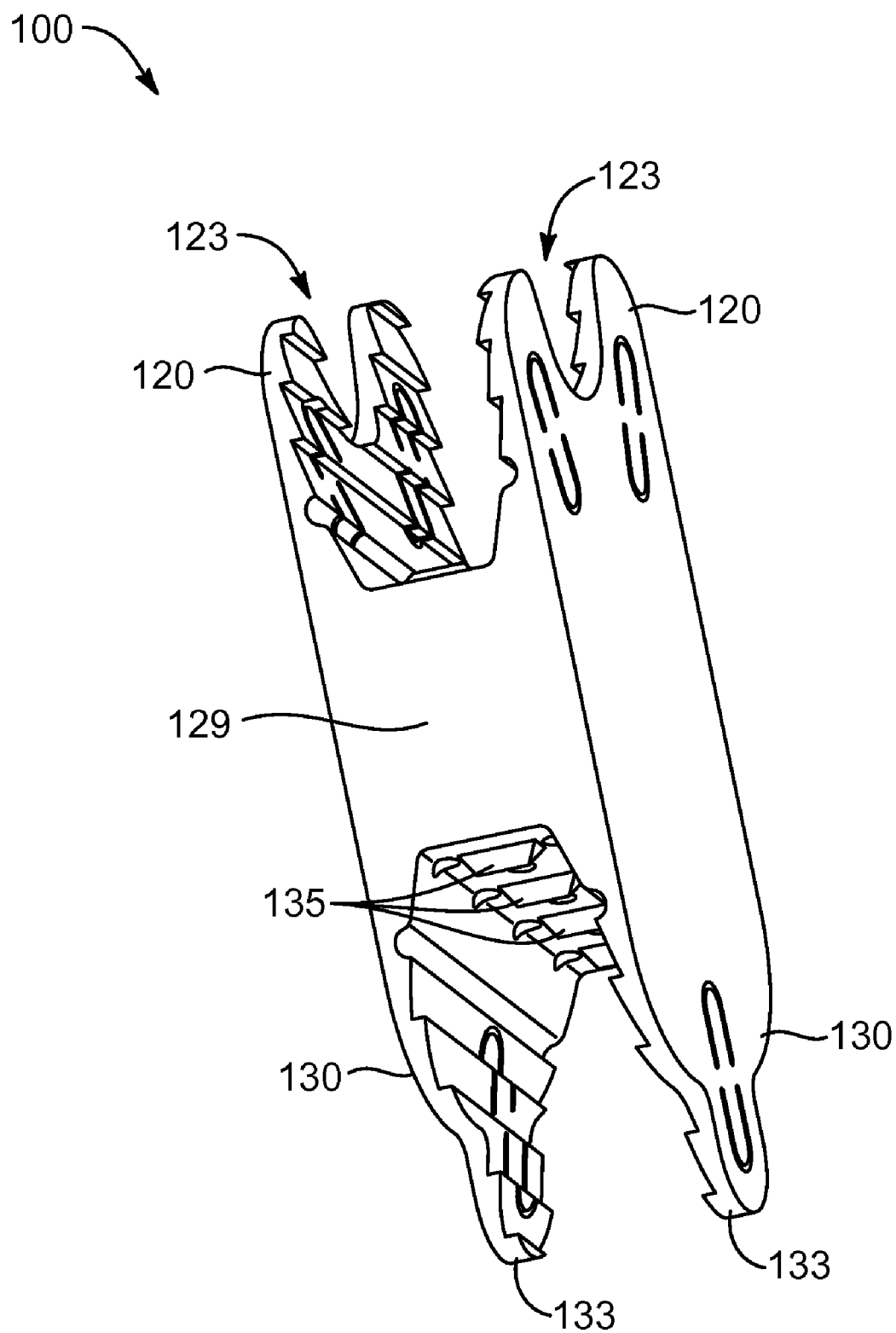
Figure 4:
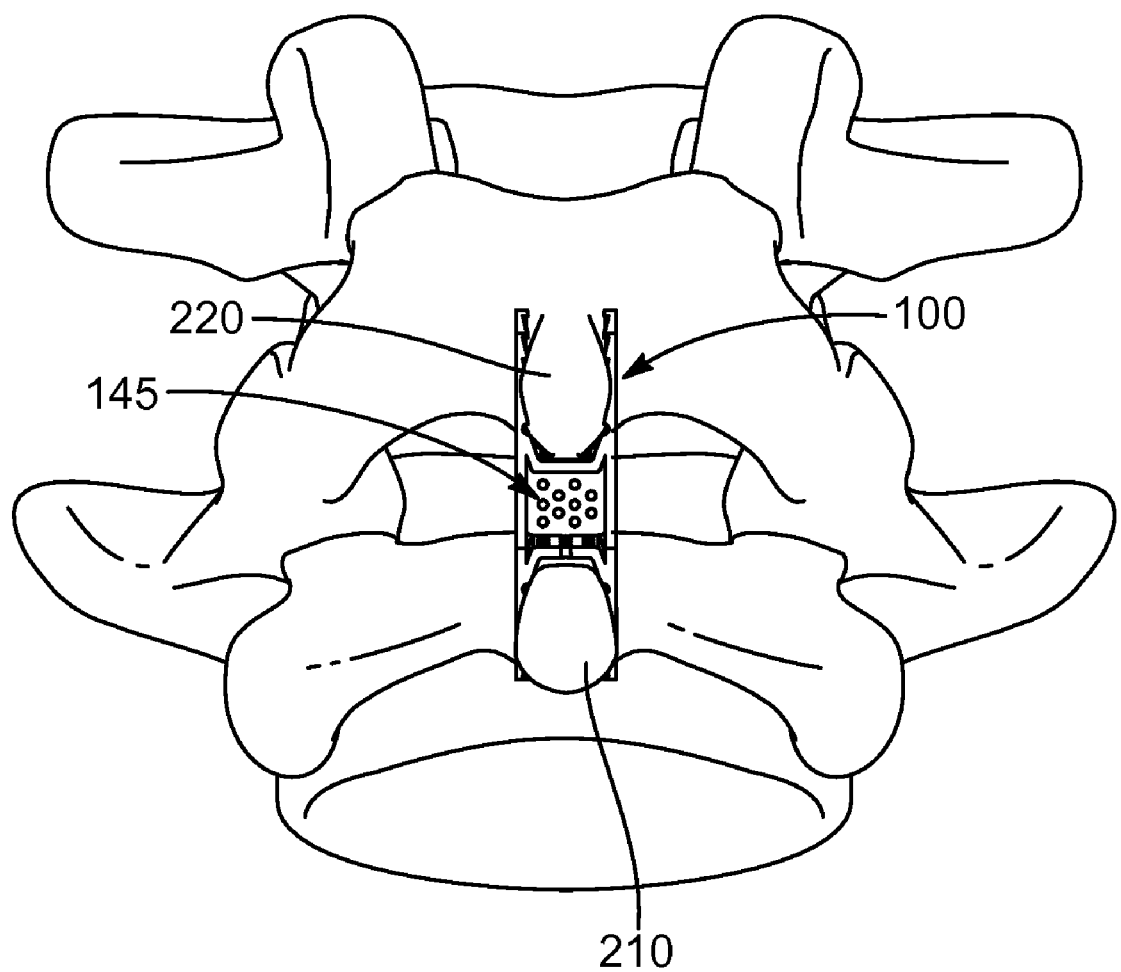
Figure 5:
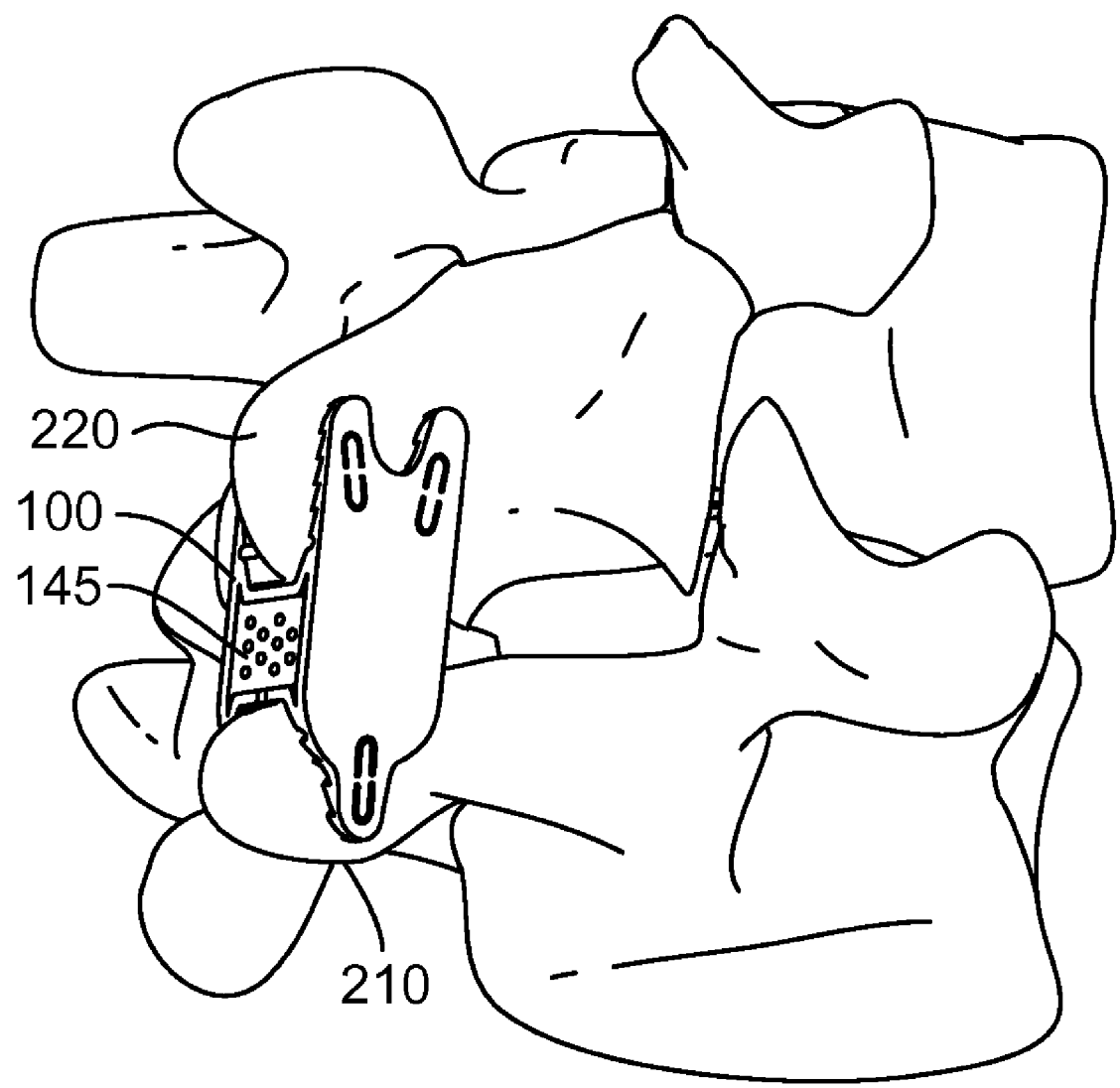
Figure 6:
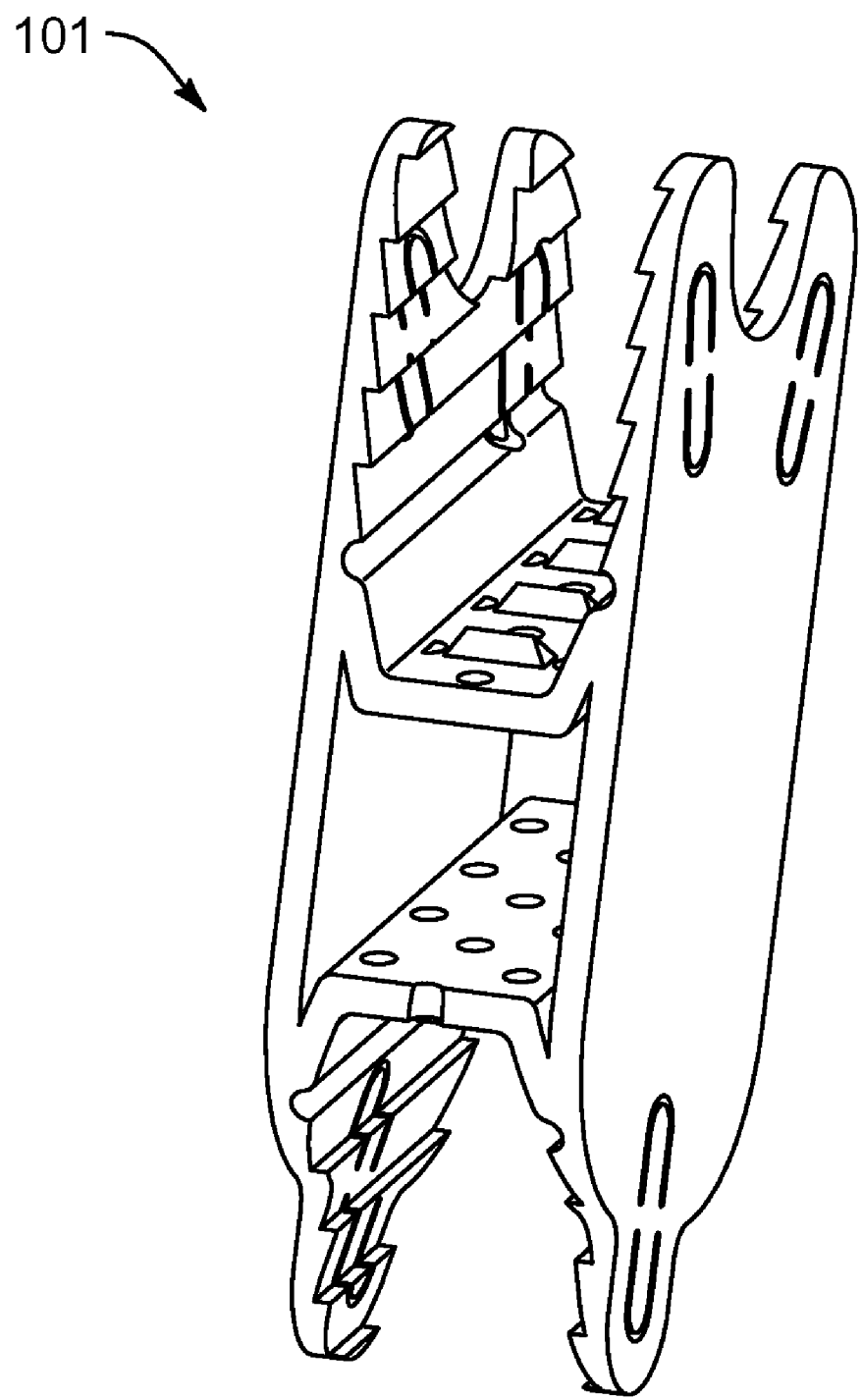
Figure 7:
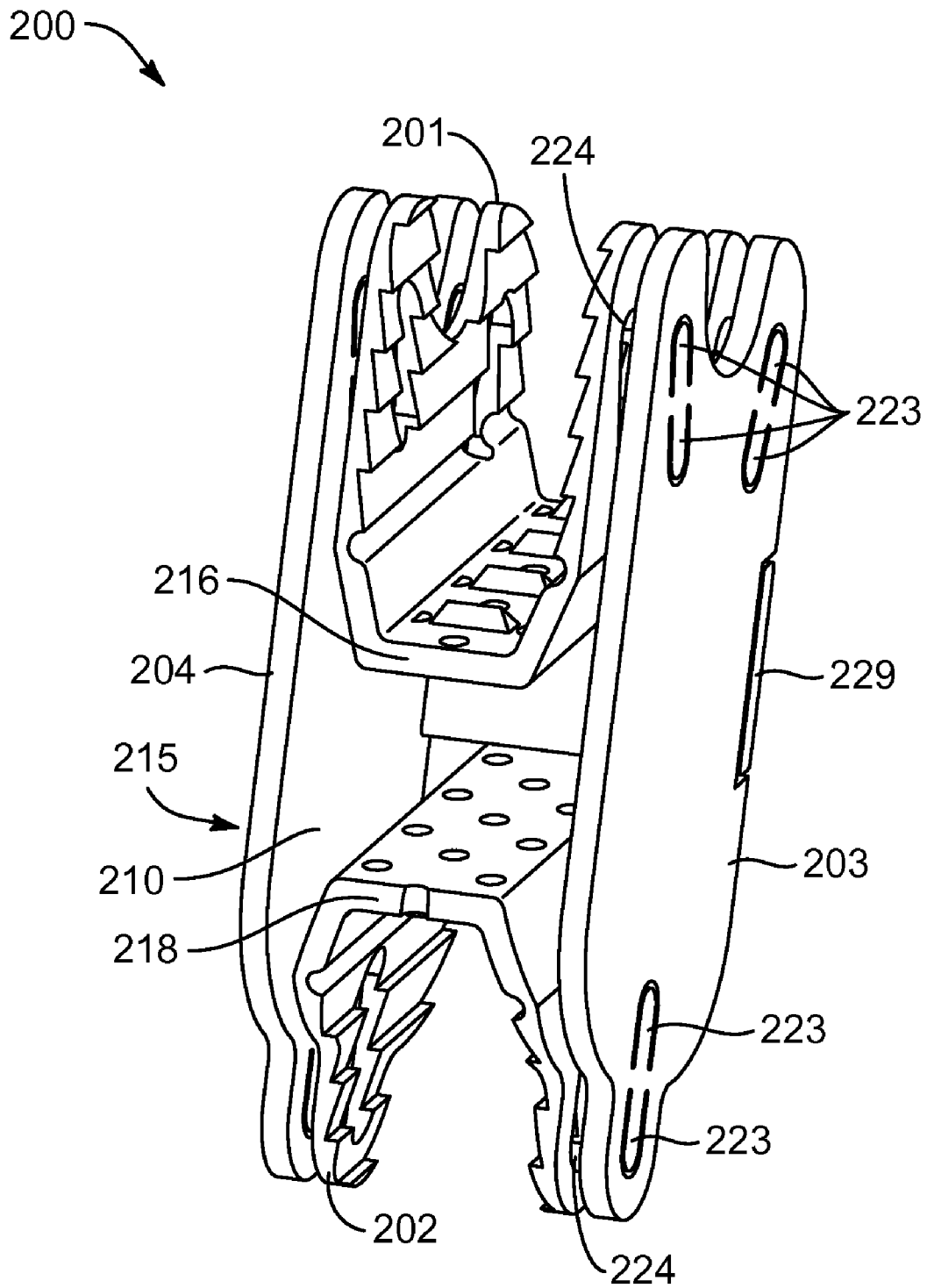
Figure 8:
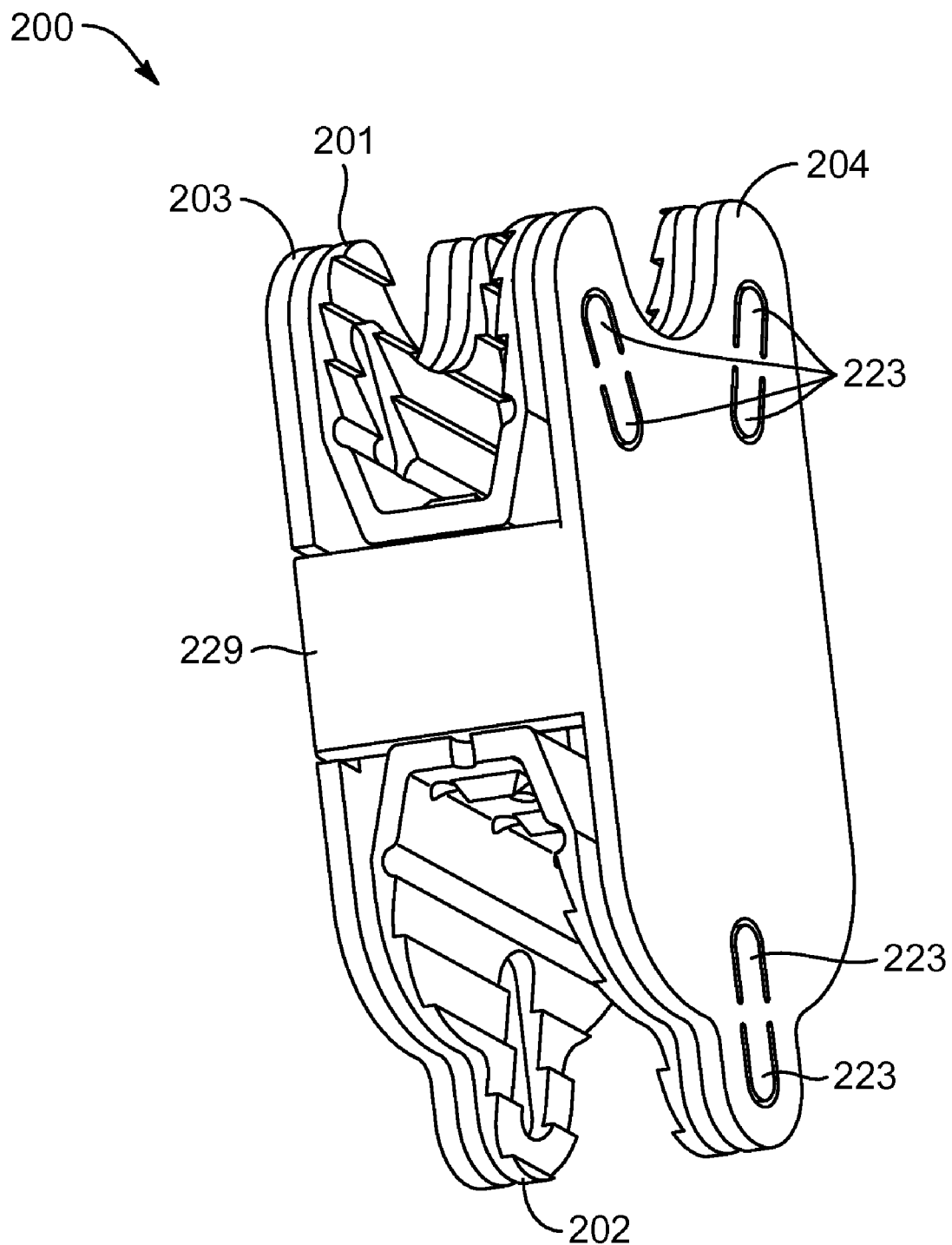
Figure 9:
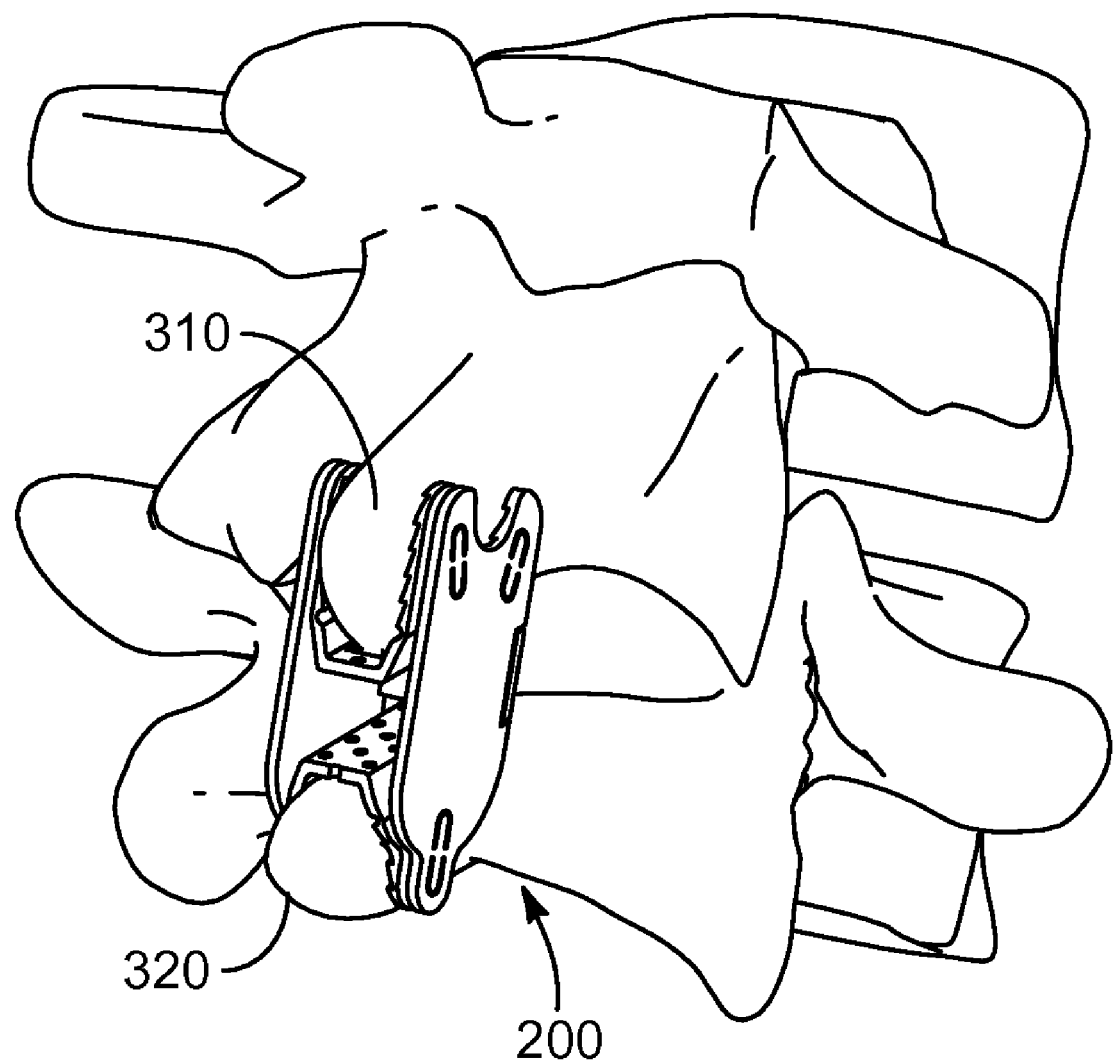
Figure 10:
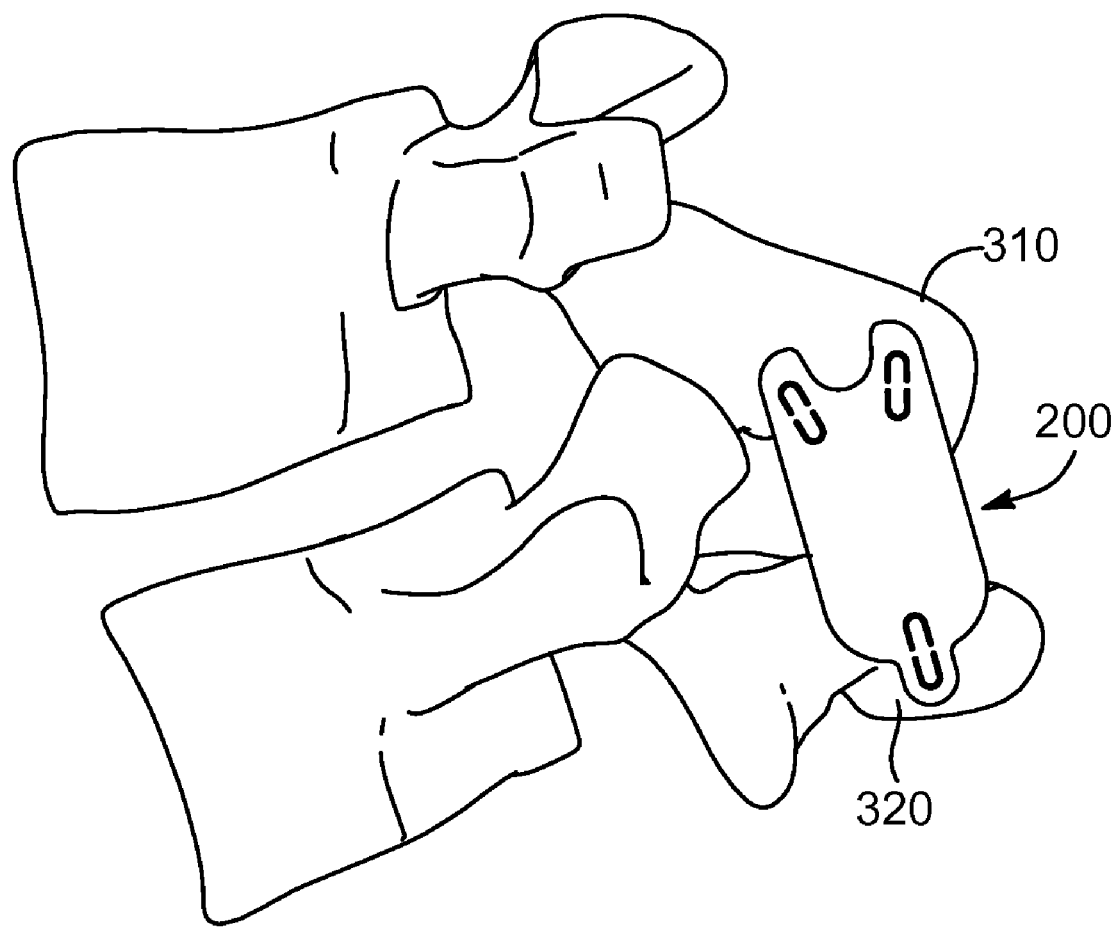
Figure 11:
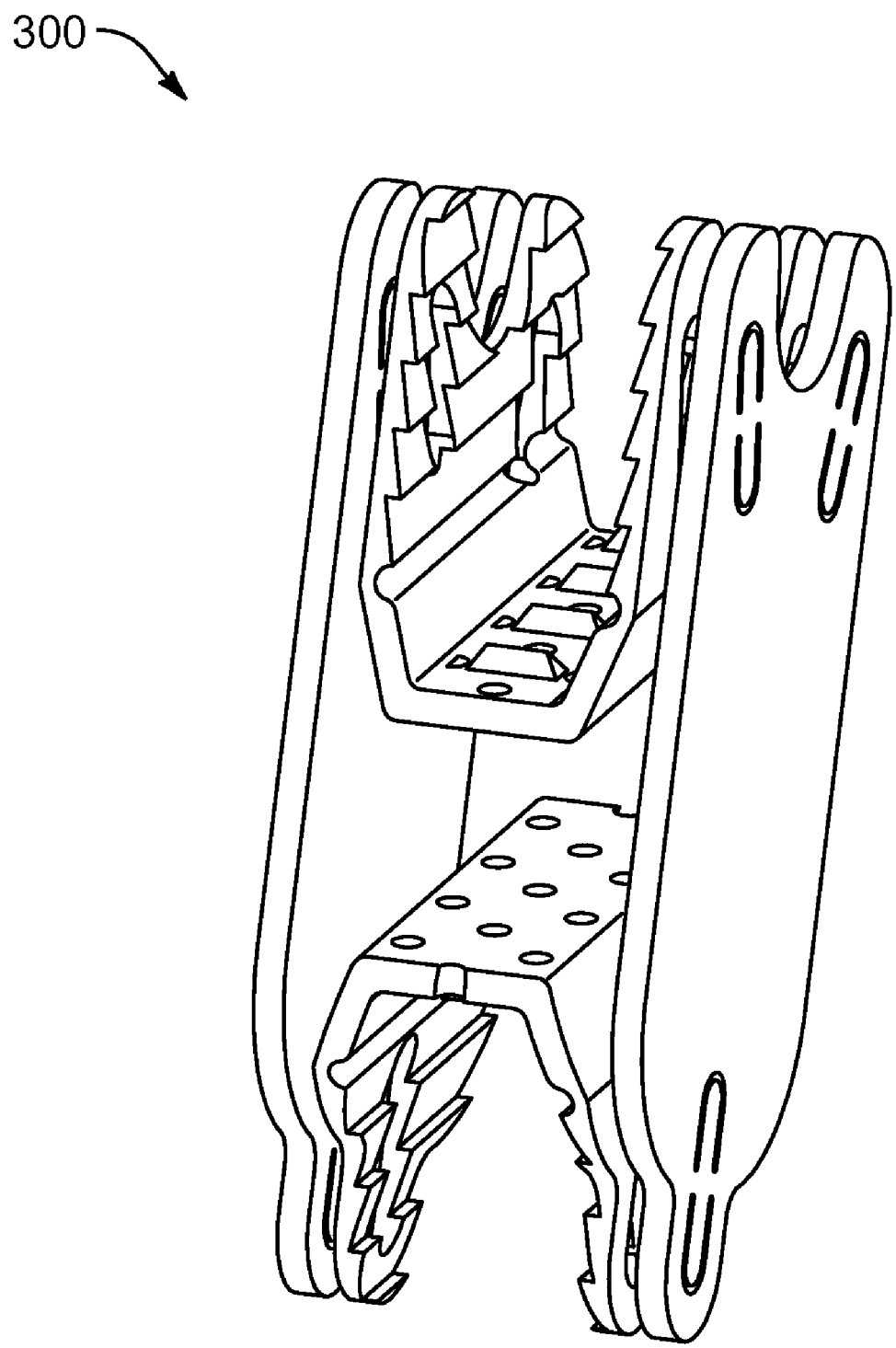
Figure 12:
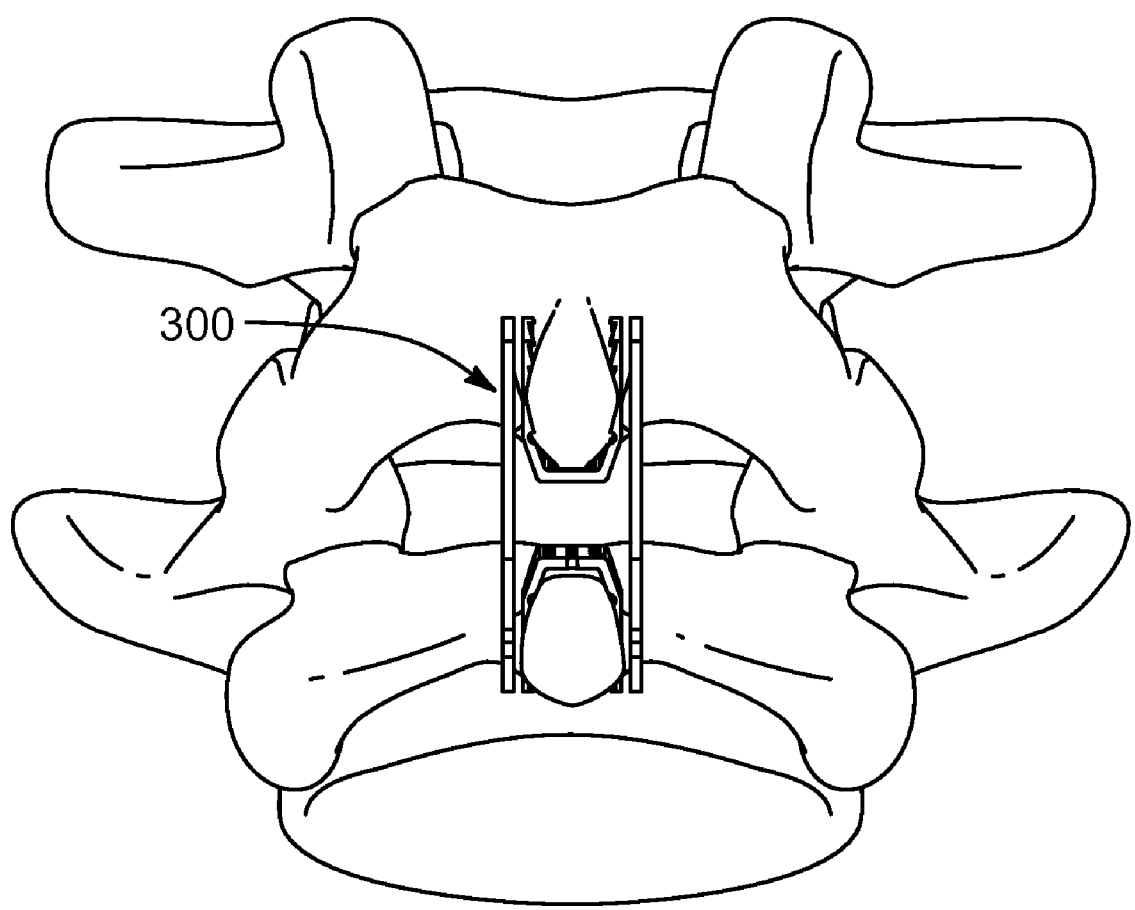
Figure 13:
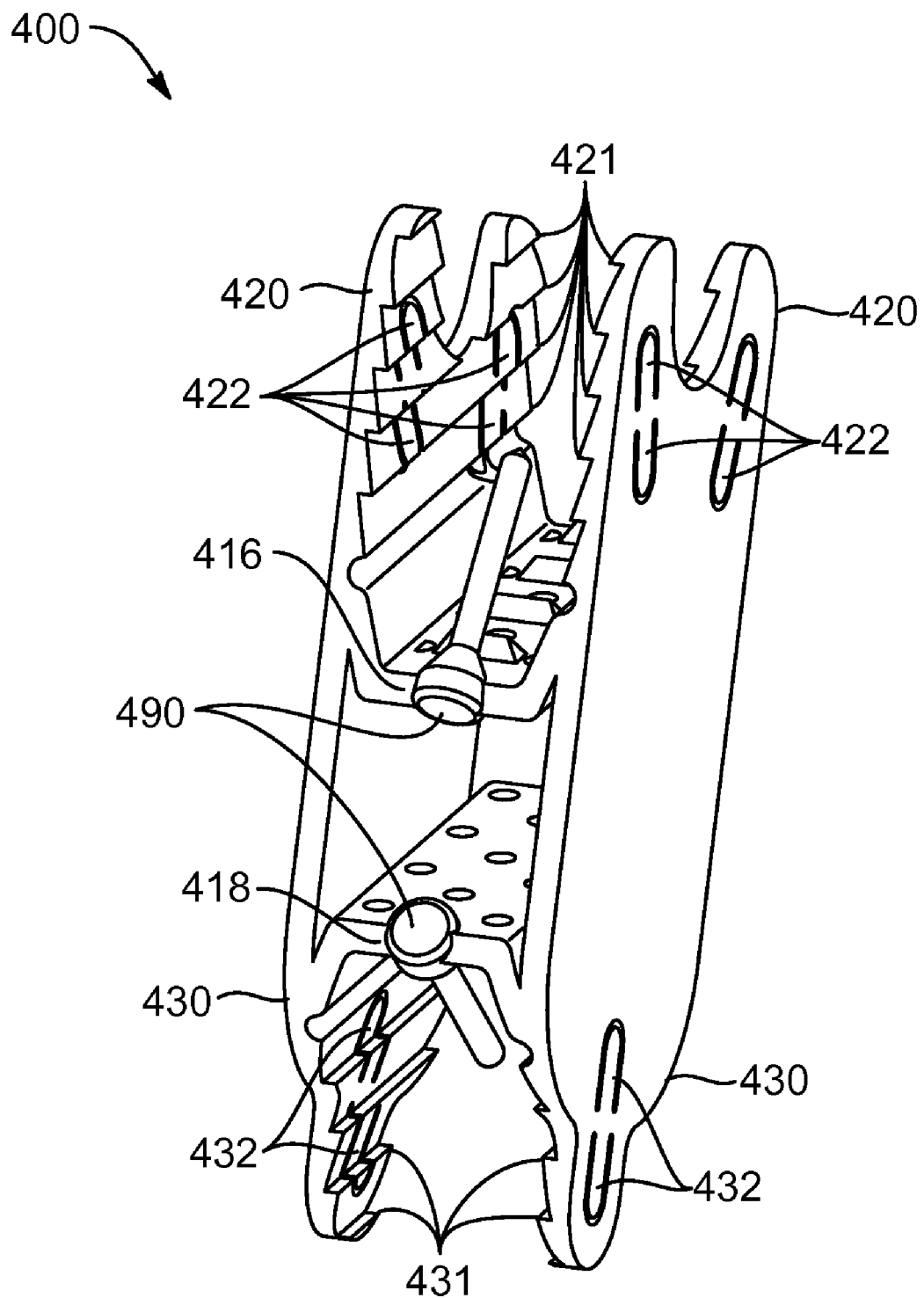
Figure 14:
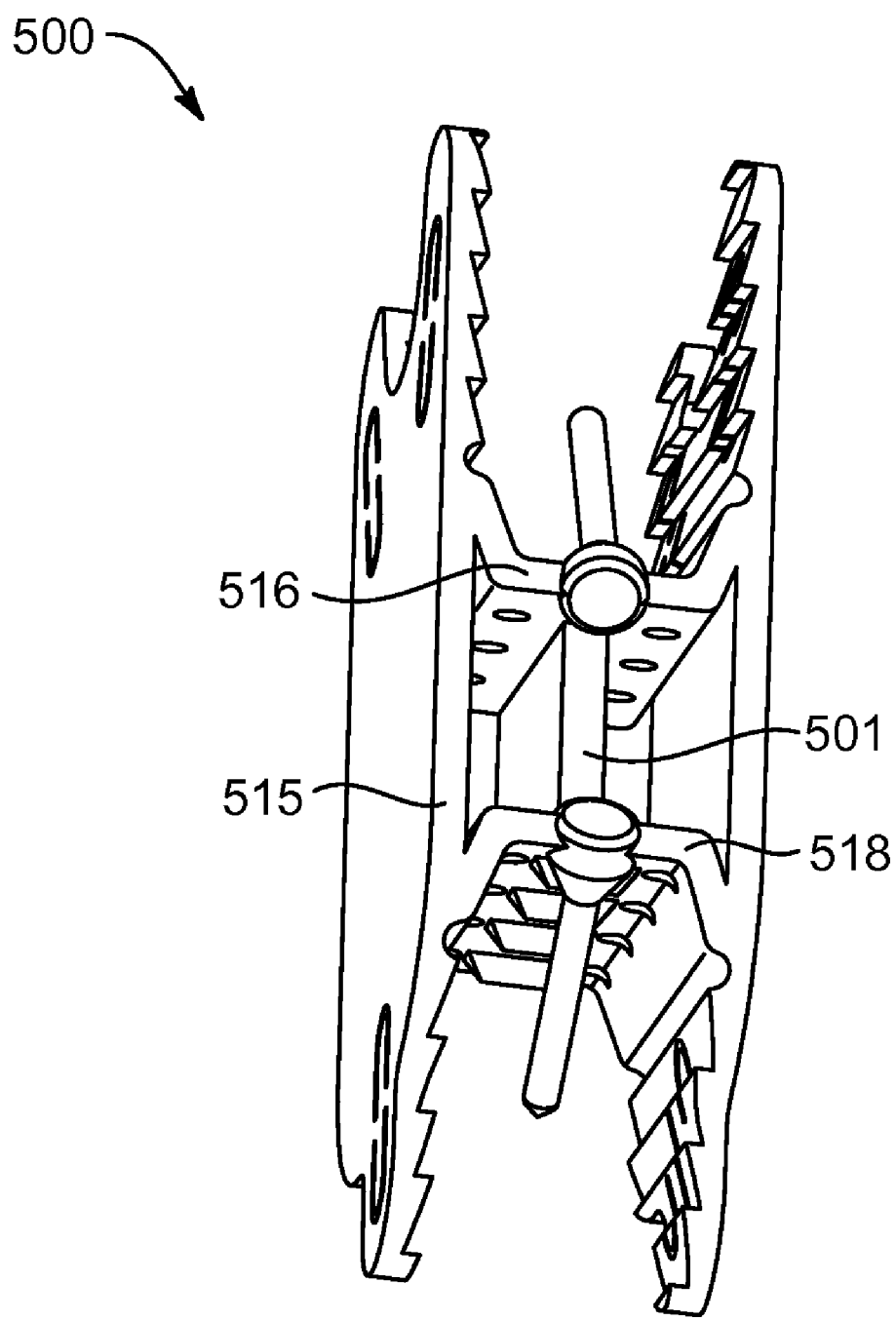
Figure 15:
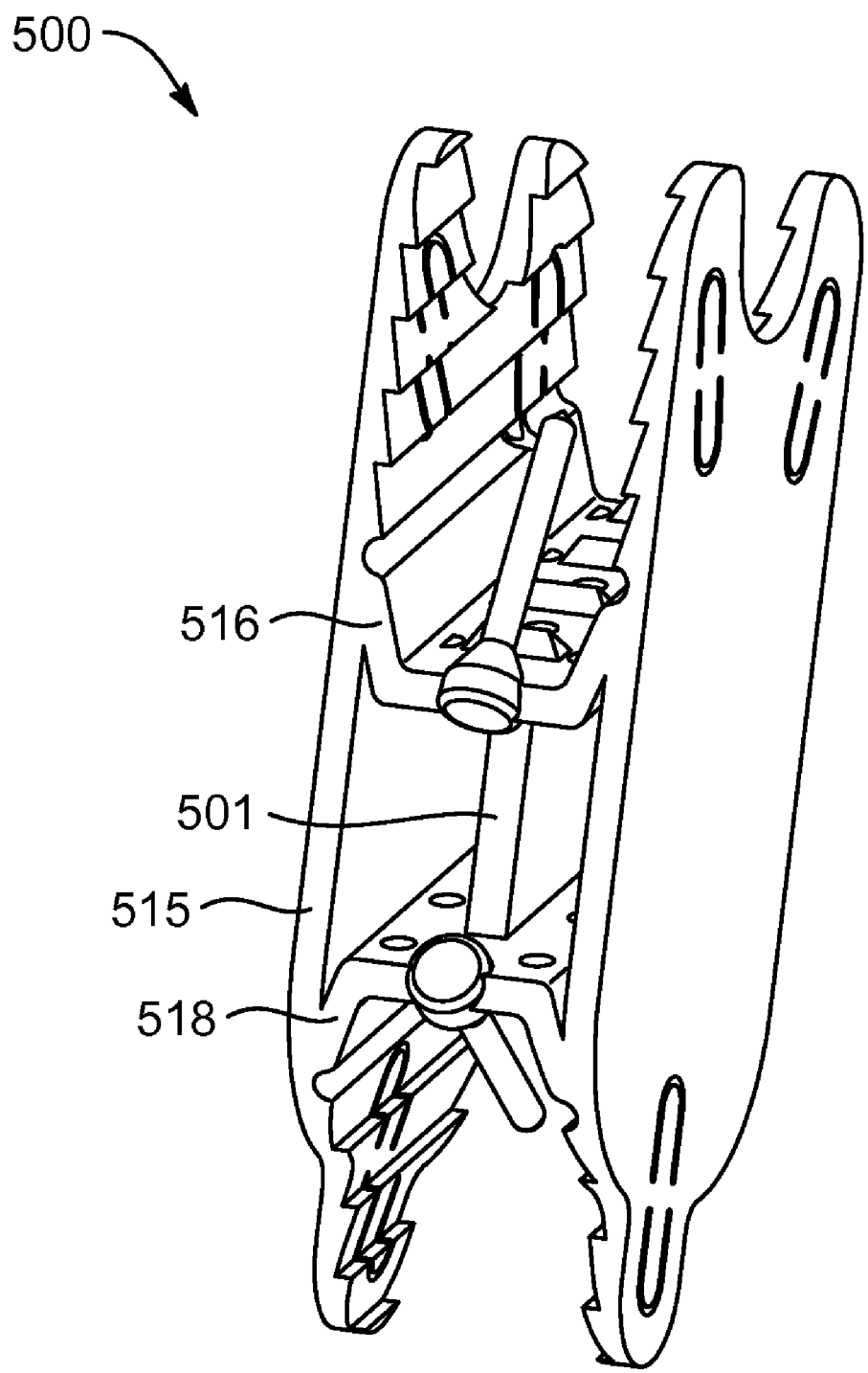
Figure 16:
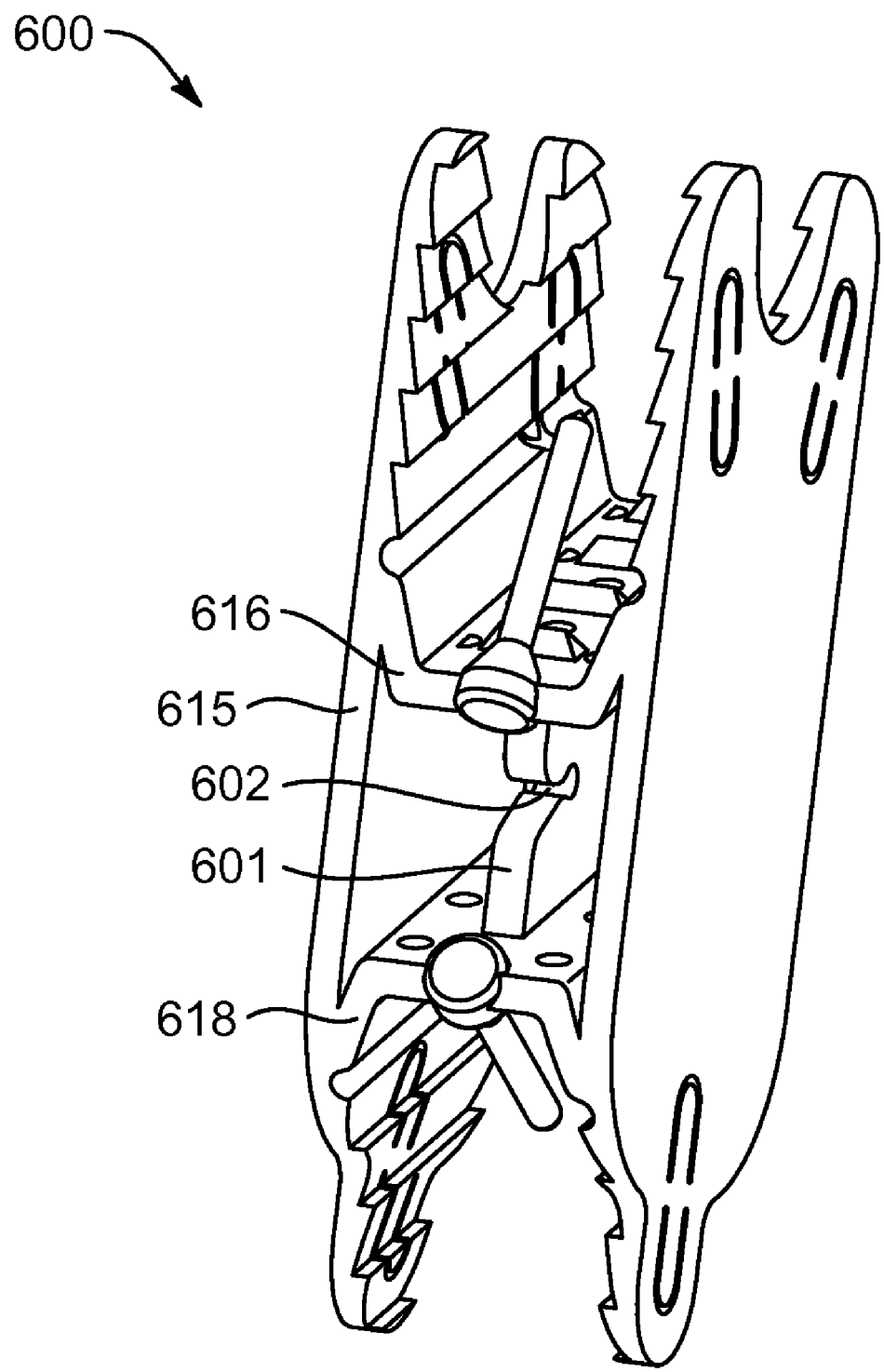
Figure 17:
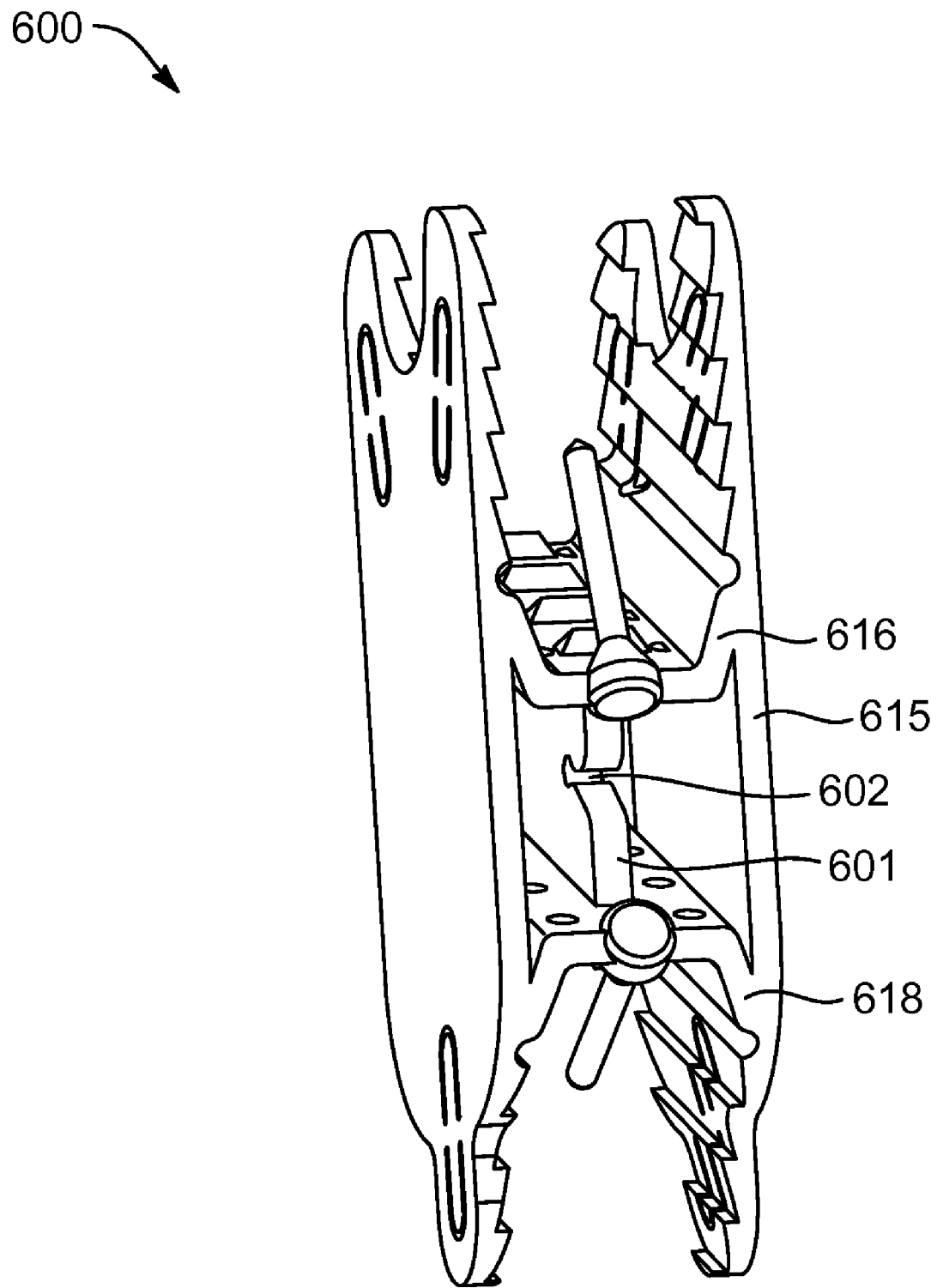

FIG. 1 is a first upper perspective view of a fusion member according to a first exemplary embodiment of the present disclosure;

FIG. 2 is an upper perspective view of the embodiment of FIG. 6;

FIG. 3 is a lower perspective view of the embodiment of FIG. 1;

FIG. 4 is an upper view of the embodiment of FIG. 1 in an installed position;

FIG. 5 is an upper perspective view of the embodiment of FIG. 1 in an installed position;

FIG. 6 is an upper perspective view of a fusion member according to a second exemplary embodiment of the present disclosure;

FIG. 7 is an upper perspective view of a fusion member according to a third exemplary embodiment of the present disclosure;

FIG. 8 is a lower perspective view of the embodiment of FIG. 7;

FIG. 9 is an upper perspective view of the embodiment of FIG. 7 in an installed position;

FIG. 10 is an side view of the embodiment of FIG. 7 in an installed position;

FIG. 11 is an upper perspective view of a fusion member according to a fourth exemplary embodiment of the present disclosure;

FIG. 12 is an upper view of the embodiment of FIG. 11 in an installed position;

FIG. 13 is an upper perspective view of a fusion member according to a fifth exemplary embodiment of the present disclosure;

FIG. 14 is an upper perspective view of a fusion member according to a sixth exemplary embodiment of the present disclosure;

FIG. 15 is a lower perspective view of the embodiment of FIG. 14;

FIG. 16 is an upper perspective view of a fusion member according to a seventh exemplary embodiment of the present disclosure; and FIG. 17 is a lower perspective view of the embodiment of FIG. 16.

DETAILED DESCRIPTION

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

Referring initially to FIGS. 1 and 3-5, an exemplary embodiment of a fusion member 100 comprises a cage 115 defining an inner volume 110 and paired extensions 120 and 130 extending from cage 115. FIGS. 4 and 5 illustrate fusion member 100 installed between a pair of spinous processes 210 and 220. As shown in FIG. 4, fusion member 100 generally forms an "H" shape in a posterior view, with extensions 120 forming ascending legs of the "H" shape and extensions 130 forming descending legs of the "H" shape. As used herein, the term "fusion member" is used to describe a member configured to promote fusion of vertebral processes.

In the embodiment shown, extensions 120 and 130 are configured so that they can be crimped (e.g., plastically deformed) onto spinous processes 210 and 220. Extensions 120 and 130 comprise gripping members 121 and 131, respectively, which assist in clamping fusion member 100 to spinous processes 210 and 220. The cage 115 may comprise gripping members 135 located between extensions 120 and 130.

Gripping members 121 and 131 allow fusion member 100 to be installed from a posterior direction so that extensions 120 and 130 can slide anteriorly along the sides of spinous processes 210 and 220. After fusion member 100 has been properly located between spinous processes 210 and 220, extensions 120 and 130 can be deformed so that gripping members 121 and 131 engage spinous processes 210 and 220. Specifically, extensions 120 can be crimped or deformed so that they are pinched toward each other so that gripping members 121 sink into spinous process 220. Similarly, extensions 130 can be crimped or deformed so that they are pinched toward each other to engage spinous process 210.

In this exemplary embodiment, gripping members 121, 131, and 135 are configured as sharp angled projections (e.g., teeth). In certain embodiments, gripping members 121, 131, and 135 may be configured as prongs, tines, tabs, barbs or spikes. In the embodiment shown, gripping members 121 and 131 are angled so that the projections point towards cage 115. Gripping members 121 and 131 are configured to allow translation between the fusion member 100 and a spinous process if the fusion member 100 is moved toward the engaged spinous process. This configuration restricts translation of the fusion member 100 in a direction away from the engaged spinous process. In the embodiment shown, gripping members 135 are pointed superiorly and inferiorly, and are configured to prevent translation in the posterior direction between the fusion member 100 and spinous processes 210 and 220.

Extensions 120 and 130 also comprise tabs 122 and 132, respectively, which assist in maintaining a fixed engagement between fusion member 100 and spinous processes 210 and 220. In certain embodiments, tabs 122 and 132 may be formed by removing material from extensions 120 and 130 in a pattern that forms tabs 122 and 132.

As shown in FIGS. 1 and 3-5, tabs 122 and 132 are in an undeformed condition wherein tabs 122 and 132 are parallel to extensions 120 and 130. After fusion member 100 is inserted between spinous processes 210 and 220, tabs 122 and 132 may be deformed (e.g., plastically deformed inward toward the space between extensions 120 and 130) so that tabs 122 and 132 further engage spinous processes 210 and 220. Tabs 122 and 132 may be deformed with a tool (e.g., forceps or a plier-type device, not shown) that comprise projections configured to engage tabs 122 and 132 and leverage members to provide easier deformation of the tabs. Tabs 122, 132 and gripping members 121, 131 serve to provide a positive engagement of fusion member 100 to spinous processes 210 and 220. In certain embodiments, fusion member 100 can provide fixation of spinous processes 210 and 220.

Cage 115 is shown in this embodiment to comprise a first end 116, a second end 118, a first side 117 and a second side 119. Cage 115 also comprise a lower surface 129, or lower cover, extending between first and second ends 116, 118 and first and second sides 117, 119. As explained in more detail below, lower surface 129 can assist in retaining bone fragments inserted into inner volume 110.

A plurality of bone fragments 145 (only a portion of which are shown in FIGS. 4 and 5) may be disposed within inner volume 110 to assist in fusing spinous processes 210 and 220 together. Cage 115 comprises a plurality of apertures 125 to promote fusion of the bone fragments 145 and spinous processes 210 and 220. In the exemplary embodiment shown, bone fragments 145 may be used to assist in inter-spinous process fusion. In other embodiments, bone fragments 145 may be used to assist in fusing various locations of adjacent vertebrae, including for example, inter-laminar fusion, facet fusion, inter-transverse process fusion, and inter-discal fusion. Bone fragments 145 may be of various sizes and shapes and may comprise bone autograft, allograft, or synthetic bone.

In the exemplary embodiment shown, extensions 120 comprise a recessed portion 123 in the area distal from cage 115. Extensions 130 comprise projections 133 in the area distal from cage 115. In certain embodiments, it may be desirable to utilize more than one fusion member 100. In such embodiments, the fusion members 100 can be arranged so that projections 133 fit into recessed portions 123. This can allow for closer spacing of fusion members 100.

Referring now to FIGS. 2 and 6, another embodiment of a fusion member 101 is equivalent to fusion member 100 shown and described above in FIGS. 1 and 3-5. Fusion member 101, however, does not comprise a lower surface 129. Still other exemplary embodiments may comprise a design similar to fusion member 100 with an additional upper surface, or upper cover, opposite of lower surface 129 to form a cage 115 that completely encloses the interior volume 110. The upper surface may be movable or installable to provide at least temporary access to the interior volume 110.

Referring now to FIGS. 7-10, an exemplary embodiment comprises a multi-piece fusion member 200. In this embodiment fusion member 200 comprises four separate components that can be assembled to form a unit that functions similar to previously-described fusion member 100. Fusion member 200 comprises a first clamping member 201, a second clamping member 202, a first plate 203, and a second plate 204. First plate 203 comprises a plurality of tabs 223 and second plate 204 comprises a plurality of tabs 233. When deformed, tabs 223 and 233 are configured to extend through slots 224 in first and second clamping members 201 and 202, respectively, and engage spinous processes 310 and 320 (shown in FIGS. 9 and 10). This configuration allows for first and second plates 203, 204 to remain coupled to first and second clamping members 201 and 202. First and second plates 203, 204 and first and second clamping members 201 and 202 may also comprise coupling or receiving members (not shown) including without limitation, threaded members, pins, eyelets, etc.

First clamping member 201 comprises a first end 216 and second clamping member comprises a second end 218. First end 216, second end 218, and the central portions of first plate 203 and second plate 204 combine to form a cage 215 defining an inner volume 210. Second plate 204 comprises a lower surface 229 (clearly visible in FIG. 8) configured to extend towards first plate 203. Lower surface 229 functions similar to previously described lower surface 129 of fusion member 100 and can serve to retain bone fragments 145 (not shown).

Referring now to FIGS. 11-12, another exemplary embodiment comprises a multi-piece fusion member 300 that is generally equivalent to the embodiment shown and described in FIGS. 7-10. This embodiment, however does not comprise a lower surface similar to lower surface 229 of the embodiment in FIGS. 7-10. As shown in FIG. 12, fusion member 300 is viewed from above in an installed position. Fusion member 300 is generally "H"-shaped when viewed from above.

Referring now to FIG. 13, another exemplary embodiment comprises a fusion member 400 similar to the one shown and described in FIGS. 1 and 3-5. This embodiment also comprises fastening members 490 configured to extend through first end 416 and second end 418 of cage 415. Fastening members 490 may comprise nails, screws, spikes, barbs, etc., and are configured to engage a spinous process inserted between extensions 420 and 430. Fastening members 490 can provide fixation of the fusion member 400 to the spinous processes in addition to that provided by gripping members 421 and 431 and tabs 422 and 432. Fastening member 490 may be preferentially positioned along a mid-sagittal plane bisecting the spinous process.

Referring now to FIGS. 14 and 15 another exemplary embodiment comprises a fusion member 500 similar to the one shown and described in FIG. 13. This embodiment comprises a septum or rib 501 extending between first end 516 and second end 518 of cage 515. Rib 501 can serve to provide structural rigidity to fusion member 500.

Referring now to FIGS. 16 and 17 another exemplary embodiment comprises a fusion member 600 similar to the one shown and described in FIGS. 14 and 15. This embodiment comprises a septum or rib 601 extending between first end 616 and second end 618 of cage 615. Rib 601 can serve to provide structural rigidity to fusion member 600. Rib 601 also comprises a receiving or securing feature 602. In the embodiment shown, securing feature 602 comprises a notch, but other exemplary embodiments may comprise different configurations, including for example, a pin, a hook, a spike, a barb, etc. Securing feature 602 can be configured to secure, for example, a shaped bone block (not shown) configured for insertion into cage 615.

Fusion members according to exemplary embodiments may be manufactured from suitable medical-grade materials, including, but not limited to, titanium and stainless steel.

It should be understood that the present system, kits, apparatuses, and methods are not intended to be limited to the particular forms disclosed. Rather, they are to cover all modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. An H-shaped fusion member for fusing a first vertebral process on a first vertebra to a second vertebral process on a second vertebra, wherein the second vertebral process is adjacent to the first vertebral process, comprising:
   a cage forming a cross bar of the H-shape;
   first and second plates projecting from the cage, the first and second plates forming a pair of ascending legs of the H-shape, wherein the first and second plates are deformable to pinch the first vertebral process;
   third and fourth plates projecting from the cage, the third and fourth plates forming a pair of descending legs of the H-shape, wherein the third and fourth plates are deformable to pinch the second vertebral process; and a first tab integrally formed within at least one of the first, second, third and fourth plates, wherein the tab is integral with the at least one plate along a first side, wherein a slit separates all remaining sides of the tab from the at least one plate, wherein the first tab is deformable to protrude from the at least one plate to penetrate at least one of the first and second vertebral processes.

2. The fusion member of claim 1, wherein the fusion member is formed as a unitary structure.

3. The fusion member of claim 1, wherein the fusion member comprises modular components.

4. The fusion member of claim 1, wherein the first and second vertebral processes are first and second spinous processes, respectively.

5. The fusion member of claim 1, wherein the cage comprises a plurality of apertures.

6. The fusion member of claim 1, wherein, after deformation, the tab points toward the cage.

7. The fusion member of claim 1, wherein, after deformation, the tab points away from the cage.

8. The fusion member of claim 1, wherein the first plate terminates with a first notch opposite the cage, wherein the second plate terminates with a second notch opposite the cage, wherein the third plate terminates with a narrow first protrusion opposite the cage, wherein the fourth plate terminates with a narrow second protrusion opposite the cage, wherein the first and second notches are complementary, with clearance, to the first and second protrusions, respectively.

9. The fusion member of claim 1, wherein the cage comprises an opening extending from a first open end of the cage to a second open end of the cage opposite the first open end, wherein, when the first vertebral process is pinched between the first and second plates and the second vertebral process is pinched between the third and fourth plates, the second open end of the cage is axial to the first open end of the cage.

10. The fusion member of claim 9, wherein the cage comprises a rib extending across the opening and between the first open end and the second open end.

11. The fusion member of claim 9, comprising a movable first cover over the first open end of the cage.

12. The fusion member of claim 9, comprising a second cover over the second open end of the cage.

13. The fusion member of claim 9, wherein the cage comprises a graft securing feature formed within the opening.

14. The fusion member of claim 13, wherein the graft securing feature is selected from the group consisting of a notch, a pin, a hook, a spike, and a barb.

15. The fusion member of claim 1, further comprising gripping members formed on the first, second, third, and fourth plates, wherein, when the first and second vertebral processes are pinched between the first, second, third, and fourth plates, respectively, the gripping members sink into the vertebral processes.

16. The fusion member of claim 15, wherein the gripping members point toward the cage.

17. An H-shaped fusion member for fusing a first vertebral process on a first vertebra to a second vertebral process on a second vertebra, wherein the second vertebral process is adjacent to the first vertebral process, comprising:
a cage forming a cross bar of the H-shape;
first and second plates projecting from the cage, the first and second plates forming a pair of ascending legs of the H-shape, wherein the first and second plates are bendable to grip the first vertebral process;
third and fourth plates projecting from the cage, the third and fourth plates forming a pair of descending legs of the H-shape, wherein the third and fourth plates are bendable to grip the second vertebral process; and
a first fastener extending from the cage, the first fastener located between at least one of the pair of ascending legs and the pair of descending legs, the first fastener securable to at least one of the first and second vertebral processes;
the fusion member further comprising first, second, third, and fourth tabs integrally formed within the first, second, third, and fourth plates, respectively, wherein the first, second, third, and fourth tabs are integral with the first, second, third, and fourth plates, respectively, along a first side of each tab, wherein a slit separates all remaining sides of each tab from the corresponding plate, wherein each tab is deformable to protrude from the corresponding plate to penetrate the corresponding vertebral process.

18. The fusion member of claim 17, wherein the fusion member is formed as a unitary structure.

19. The fusion member of claim 17, wherein the fusion member comprises modular components.

20. The fusion member of claim 17, wherein the first and second vertebral processes are first and second spinous processes, respectively, wherein the first and second spinous processes are bisected by a mid-sagittal plane, wherein, when the first fastener is secured to the at least one vertebral process, the first fastener is positioned along the mid-sagittal plane.

21. The fusion member of claim 17, wherein the first fastener is selected from the group consisting of nails, screws, spikes, and barbs.

22. The fusion member of claim 17, wherein the cage comprises an opening extending from a first open end of the cage to a second open end of the cage opposite the first open end, wherein, when the first vertebral process is pinched between the first and second plates and the second vertebral process is pinched between the third and fourth plates, the second open end of the cage is axial to the first open end of the cage.

23. The fusion member of claim 22, comprising a movable first cover over the first open end of the cage.

24. The fusion member of claim 22, comprising a second cover over the second open end of the cage.

25. The fusion member of claim 22, wherein the cage comprises a graft securing feature formed within the opening.

26. The fusion member of claim 25, wherein the graft securing feature is selected from the group consisting of a notch, a pin, a hook, a spike, and a barb.

27. An H-shaped fusion member for fusing a first vertebral process on a first vertebra to a second vertebral process on a second vertebra, wherein the second vertebral process is adjacent to the first vertebral process, comprising:
a cage forming a cross bar of the H-shape, the cage comprising an opening extending along an axis from a first open end of the cage to a second open end of the cage opposite the first open end;
first and second plates projecting from the cage in a direction transverse to the axis, the first and second plates forming a pair of ascending legs of the H-shape, wherein the first and second plates are crimpable to compress the first vertebral process;
third and fourth plates projecting from the cage, the third and fourth plates forming a pair of descending legs of the H-shape, wherein the third and fourth plates are crimpable to compress the second vertebral process; and
a movable first cover over the first open end of the cage;

the fusion member further comprising at least one tab integrally formed within each of the first, second, third, and fourth plates, respectively, wherein the tabs are integral with the first, second, third, and fourth plates, respectively, along a first side of each tab, wherein a slit separates all remaining sides of each tab from the corresponding plate, wherein each tab is deformable to protrude from the corresponding plate to penetrate the corresponding vertebral process.

28. The fusion member of claim 27, wherein the fusion member is formed as a unitary structure.

29. The fusion member of claim 27, wherein the fusion member comprises modular components.

30. The fusion member of claim 27, wherein the first and second vertebral processes are first and second spinous processes, respectively.

31. The fusion member of claim 27, wherein the first cover is movable between a closed position in which the first cover blocks the first open end of the cage, and an open position in which the first cover is displaced from the first open end of the cage to provide access therethrough.

32. The fusion member of claim 27, comprising a second cover over the second open end of the cage.

33. The fusion member of claim 27, wherein the cage comprises a graft securing feature formed within the opening.

34. The fusion member of claim 33, wherein the graft securing feature is selected from the group consisting of a notch, a pin, a hook, a spike, and a barb.

35. An H-shaped fusion member for fusing a first vertebral process on a first vertebra to a second vertebral process on a second vertebra, wherein the second vertebral process is adjacent to the first vertebral process, comprising:
a cage forming a cross bar of the H-shape;
first and second plates projecting from the cage, the first and second plates forming a pair of ascending legs of the H-shape, wherein the first and second plates are deformable to clamp the first vertebral process;
third and fourth plates projecting from the cage, the third and fourth plates forming a pair of descending legs of the H-shape, wherein the third and fourth plates are deformable to clamp the second vertebral process; and
a graft securing feature formed within the cage;
the fusion member further comprising at least one tab integrally formed within each of the first, second, third, and fourth plates, respectively, wherein the tabs are integral with the first, second, third, and fourth plates, respectively, along a first side of each tab, wherein a slit separates all remaining sides of each tab from the corresponding plate, wherein each tab is deformable to protrude from the corresponding plate to penetrate the corresponding vertebral process.

36. The fusion member of claim 35, wherein the fusion member is formed as a unitary structure.

37. The fusion member of claim 35, wherein the fusion member comprises modular components.

38. The fusion member of claim 35, wherein the first and second vertebral processes are first and second spinous processes, respectively.

39. The fusion member of claim 35, wherein the graft securing feature is selected from the group consisting of a notch, a pin, a hook, a spike, and a barb.

40. The fusion member of claim 35, comprising a movable first cover over the first open end of the cage.

41. The fusion member of claim 35, comprising a second cover over the second open end of the cage.

42. A fusion member for fusing a first vertebral process on a first vertebra to a second vertebral process on a second vertebra, wherein the second vertebral process is adjacent to the first vertebral process, comprising:
a first clamping member, wherein the first clamping member comprises a channel;
a second clamping member like the first clamping member, wherein the second clamping member is disposed in back to back relationship with the first clamping member and spaced apart therefrom;
a first plate secured to a first side of the first and second clamping members; and
a second plate secured to a second side of the first and second clamping members;
wherein the first clamping member, the first plate, and the second plate each terminate with a first notch opposite the second clamping member, wherein the second clamping member, the first plate, and the second plate each terminate with a first protrusion opposite the first clamping member, wherein the first notch is complementary to the first protrusion with clearance therebetween;
wherein, when the first and second vertebral processes are positioned within the first and second clamping members, respectively, the fusion member is permanently deformable to pinch the first and second vertebral processes.

43. The fusion member of claim 42, wherein the first and second vertebral processes are first and second spinous processes, respectively.

44. The fusion member of claim 42, wherein each of the first and second clamping members comprises a plurality of apertures, wherein, when the first and second vertebral processes are pinched between the first and second clamping members, the apertures are proximate the vertebral processes.

45. The fusion member of claim 42, comprising a cover secured to one of the first and second plates, the cover extending between the first and second plates, the cover extending between the first and second clamping members.

46. The fusion member of claim 42, further comprising gripping members formed on the first and second clamping members, wherein, when the first and second vertebral processes are pinched between the first and second clamping members, respectively, the gripping members sink into the vertebral processes.

47. The fusion member of claim 46, wherein at least a portion of the gripping members on one of the first and second clamping members point toward the other of the first and second clamping members.

48. The fusion member of claim 42, further comprising at least one tab integrally formed within each of the first and second plates, respectively, wherein each tab is deformable to protrude from the corresponding plate to penetrate the corresponding vertebral process.

49. The fusion member of claim 48, wherein the tab is integral with the corresponding plate along a first side, wherein a slit separates all remaining sides of the tab from the corresponding plate.

50. The fusion member of claim 48, wherein at least one of the first and second clamping members comprises an opening adjacent to each tab, wherein each opening is complementary to the corresponding tab with clearance therebetween.

51. The fusion member of claim 50, wherein, after deformation, each tab protrudes through the corresponding opening to secure the corresponding plate to the corresponding clamping member.

52. The fusion member of claim 42, comprising a cover secured to one of the first and second plates, the cover extending between the first and second plates, the cover extending between the first and second clamping members.

53. A fusion member for fusing a first vertebral process on a first vertebra to a second vertebral process on a second vertebra, wherein the second vertebral process is adjacent to the first vertebral process, comprising:
a first clamping member, wherein the first clamping member comprises a channel;
a second clamping member like the first clamping member, wherein the second clamping member is disposed in back to back relationship with the first clamping member and spaced apart therefrom;
a first plate secured to a first side of the first and second clamping members; and
a second plate secured to a second side of the first and second clamping members;
wherein the fusion member further comprises at least one tab integrally formed within each of the first and second plates, respectively, wherein the tab is integral with the corresponding plate along a first side, wherein a slit separates all remaining sides of the tab from the corresponding plate;
wherein, when the first and second vertebral processes are positioned within the first and second clamping members, respectively, the fusion member is permanently deformable to pinch the first and second vertebral processes and each tab is deformable to protrude from the corresponding plate to penetrate the corresponding vertebral process.

54. The fusion member of claim 53, wherein the first and second vertebral processes are first and second spinous processes, respectively.

55. The fusion member of claim 53, wherein each of the first and second clamping members comprises a plurality of apertures, wherein, when the first and second vertebral processes are pinched between the first and second clamping members, the apertures are proximate the vertebral processes.

56. The fusion member of claim 53, comprising a cover secured to one of the first and second plates, the cover extending between the first and second plates, the cover extending between the first and second clamping members.

57. The fusion member of claim 53, further comprising gripping members formed on the first and second clamping members, wherein, when the first and second vertebral processes are pinched between the first and second clamping members, respectively, the gripping members sink into the vertebral processes.

58. The fusion member of claim 57, wherein at least a portion of the gripping members on one of the first and second clamping members point toward the other of the first and second clamping members.

59. The fusion member of claim 53, wherein at least one of the first and second clamping members comprises an opening adjacent to each tab, wherein each opening is complementary to the corresponding tab with clearance therebetween.

60. The fusion member of claim 59, wherein, after deformation, each tab protrudes through the corresponding opening to secure the corresponding plate to the corresponding clamping member.

61. A fusion member for fusing a first vertebral process on a first vertebra to a second vertebral process on a second vertebra, wherein the second vertebral process is adjacent to the first vertebral process, comprising:
a first clamping member, wherein the first clamping member comprises a channel;
a second clamping member like the first clamping member, wherein the second clamping member is disposed in back to back relationship with the first clamping member and spaced apart therefrom;
a first plate secured to a first side of the first and second clamping members; and
a second plate secured to a second side of the first and second clamping members;
wherein the fusion member further comprises at least one tab integrally formed within each of the first and second plates, respectively;
wherein at least one of the first and second clamping members comprises an opening adjacent to each tab, wherein each opening is complementary to the corresponding tab with clearance therebetween;
wherein, when the first and second vertebral processes are positioned within the first and second clamping members, respectively, the fusion member is permanently deformable to pinch the first and second vertebral processes and each tab is deformable to protrude from the corresponding plate to penetrate the corresponding vertebral process.

62. The fusion member of claim 61, wherein the first and second vertebral processes are first and second spinous processes, respectively.

63. The fusion member of claim 61, wherein each of the first and second clamping members comprises a plurality of apertures, wherein, when the first and second vertebral processes are pinched between the first and second clamping members, the apertures are proximate the vertebral processes.

64. The fusion member of claim 61, further comprising gripping members formed on the first and second clamping members, wherein, when the first and second vertebral processes are pinched between the first and second clamping members, respectively, the gripping members sink into the vertebral processes.

65. The fusion member of claim 64, wherein at least a portion of the gripping members on one of the first and second clamping members point toward the other of the first and second clamping members.

66. The fusion member of claim 61, wherein, after deformation, each tab protrudes through the corresponding opening to secure the corresponding plate to the corresponding clamping member.

* * * * *